United States Patent [19]

Drysdale et al.

[11] Patent Number: 5,288,881
[45] Date of Patent: Feb. 22, 1994

[54] CONTINUOUS REDUCED PRESSURE DIMERIC CYCLIC ESTER PRODUCTION

[75] Inventors: Neville E. Drysdale; Kang Lin; Thomas W. Stambaugh, all of Newark, Del.

[73] Assignee: E. I. du Pont de Nemours and Company, Wilmington, Del.

[21] Appl. No.: 848,188

[22] Filed: Mar. 12, 1992

[51] Int. Cl.$^5$ ............................................. C07D 319/12
[52] U.S. Cl. ..................................................... 549/274
[58] Field of Search ......................................... 549/274

[56] References Cited

U.S. PATENT DOCUMENTS

| | | | |
|---|---|---|---|
| 1,095,205 | 5/1914 | Gruter | 549/274 |
| 2,668,162 | 2/1954 | Lowe | 549/274 |
| 5,023,349 | 6/1991 | Bhatia | 549/274 |
| 5,053,522 | 10/1991 | Muller | 549/274 |

*Primary Examiner*—Bernard Dentz
*Assistant Examiner*—A. A. Owens

[57] ABSTRACT

An improved process for converting oligomers of alphahydroxycarboxylic acids, such as glycolic and lactic acid, to dimeric cyclic esters, such as glycolide and lactide. The continuous process is conducted at reduced pressures and depolymerizing temperatures in a heated columnar depolymerization zone, coupled with an essentially unheated receiver for unconverted oligomer. By feeding the oligomer to the upper end of the column while coordinating the feed rate with the depolymerization temperature such that a fraction of the oligomer is converted to a vapor product stream containing the cyclic ester and another fraction of the oligomer exits the column at its lower end and passes to the receiver vessel, the dimeric cyclic ester is produced at high production rates and the oligomer is subjected to minimal thermal stress.

14 Claims, No Drawings

CONTINUOUS REDUCED PRESSURE DIMERIC CYCLIC ESTER PRODUCTION

BACKGROUND OF THE INVENTION

1. Field of the Invention

This invention relates to an improved process for converting oligomers of alpha-hydroxycarboxylic acids, such as glycolic and lactic acid, to dimeric cyclic esters, such as glycolide and lactide. More particularly, the invention relates to a continuous process conducted at reduced pressures and depolymerizing temperatures in a heated columnar depolymerization zone, coupled with an essentially unheated receiver for unconverted oligomer, whereby dimeric cyclic ester is produced at high production rates and the oligomer is subjected to minimal thermal stress.

2. Description of the Related Art

Dimeric cyclic esters of hydroxycarboxylic acids such as glycolide (1,4-dioxane-2,5-dione) and lactide (1,4-dioxane-3,6-dimethyl-2,5-dione), are intermediates to high molecular weight poly (hydroxycarboxylic acids) which may be useful in biomedical and other applications because of their ability to be degraded biologically and hydrolytically to form physiologically and environmentally acceptable by-products.

The preparation of the dimeric cyclic esters of alpha-hydroxycarboxylic acids is an old and much studied process. One such scheme comprises first preparing an oligomer of the hydroxy carboxylic acid, i.e., a relatively short-chain condensation polymer thereof, then heating the polymer under reduced pressure to generate the desired cyclic ester, see for example: Gruter et al., U.S. Pat. No. 1,095,205 (1914); Lowe, U.S. Pat. No. 2,668,162 (1954); Selman, U.S. Pat. No. 3,322,791 (1967); Schmitt et al., U.S. Pat. No. 3,597,450 (1971); and Bellis, U.S. Pat. No. 4,727,163 (1988).

The above processes, spanning over 70 years of technology, involve heating the high-boiling polymeric intermediate under distillation conditions whereby the polymer thermolizes/depolymerizes to the move volatile cyclic ester, which distills from the reaction mass. Such processes suffer in that they require hours of reaction time at high temperatures for the conversion of the polymeric intermediate to the cyclic ester. Further, the rather long residence times at the high temperatures employed often result in side reactions, leading, for example, to unwanted isomers, charring of the polymer and consequently difficult to handle reactor heels.

A more recent patent, Muller, U.S. Pat. No. 5,053,522, discloses continuous and semi-continuous processes for the preparation of L-lactide: initially a quantity of L-polylactic acid (oligomer) and catalyst are added to a reactor, the reactor is heated under reduced pressure to operating temperatures and the L-lactide formed is distilled off. After a certain quantity of the product is distilled, additional L-polylactic acid is fed to the reactor. In the continuous process mode, patentee states the feed is advantageously arranged such that the volume of the reactor contents is kept constant as far as possible. Patentee also states that where the L-polylactic acid is fed batchwise, the residual volume of the reactor contents is not critical within a wide range with respect to product quality, but that it is advantageous to top off (refill) the reactor after a conversion of 50 to 90%. He further states in this regard that "It cannot be excluded that excessive lowering of the reactor contents leads to a deterioration in the product."

The disclosed process suffers in that, in all its modes of operation, at least a significant portion of the oligomer fed to the reactor is continuously under thermal stress throughout the depolymerization step, and that this eventually results in degradation products and high-boiling residues in addition to the desired lactide. That this is so becomes apparent on considering that under the so-called depolymerizing conditions, the oligomer can not only depolymerize to the lower molecule weight and more volatile cyclic ester (lactide) but that it can continue to polymerize (with loss of water, which contaminates the cyclic ester distillate) to higher molecular weight and less volatile material.

In general, high molecular weight oligomer does not yield cyclic ester as rapidly/readily as low molecular weight material. This may be attributed to the greater viscosity of the higher molecular weight material and the lesser content of terminal hydroxy groups.

It appears that for such reason those skilled in the art prefer to employ oligomers having relatively low mean molecular weights, for example, the 400 to 2000, preferably 500 to 800 polylactic acid molecular weights of Muller above. It appears, too, that the longer the oligomeric material is subjected to the thermal stress of the depolymerization temperatures the more prone it is to decompose to acidic by-products, and to lose its ability to generate cyclic ester at practical production rates and eventually to form discolored and charred reactor residues (heels).

It is also known, as disclosed in Bhatia, U.S. Pat. No. 5,023,349, to convert oligomers of alpha-carboxylic acids (glycolic, lactic) to dimeric cyclic esters (glycolide, lactide) by continuously feeding the oligomer to the top of a columnar reaction (depolymerization) zone heated at depolymerization temperatures while passing an inert gas ($N_2$ or the like) up through the oligomeric mass to sweep the cyclic ester therefrom and form a gaseous product stream, then recovering the cyclic ester from the gaseous product stream. Any unconverted oligomer accumulates in a zone below the depolymerization zone. Although the gas-assisted process of Bhatia '349 represents a significant advance in the art in providing high conversion to and recovery of high quality dimeric cyclic ester (lactide) it has the drawback that the entraining inert gas occupies a significant portion of the reactor volume and thus limits the production rate.

SUMMARY OF THE INVENTION

It is an object of this invention to provide a continuous high production rate reduced pressure depolymerization process for the preparation of dimeric cyclic esters which does not utilize a gaseous entraining agent for the cyclic ester and which minimizes thermal stress on unconverted oligomer during the depolymerization step.

It is another object to provide such process which enables any unconverted and relatively unstressed oligomer to be recovered and recycled to the depolymerization step during the course of the reaction for the further production of dimeric cyclic ester.

It is a further object to provide processes as above wherein the oligomer is an oligomer of lactic acid, preferably L-lactic acid and the dimeric cyclic ester is lactide, preferably L-lactide.

What has been discovered is an improved process for depolymerizing an oligomer of an alpha-hydroxycarboxylic acid to a dimeric cyclic ester, which process comprises effecting the depolymerization in a continuous or semi-continuous manner under reduced pressure in the substantial absence of a gaseous entraining agent for the cyclic ester, the improvement which comprises the steps of (a) providing a multi-stage column equipped with a heating means, an oligomer feed inlet near the upper end of the column, a vapor product stream outlet above the feed inlet, and a receiver at the lower end of the column;

(b) continuously or semi-continuously feeding the oligomer to the upper end of the column;

(c) heating the column to a depolymerizing temperature;

(d) maintaining the receiver at a temperature below the depolymerization temperature;

(e) coordinating the oligomer feed rate with the depolymerization temperature such that a fraction of the oligomer is converted to a vapor product stream containing the cyclic ester and another fraction exits the column at its lower end and passes to the receiver; and, (f) removing the vapor product stream at the upper end of the column and recovering the cyclic ester therefrom.

In another aspect of the process, the receiver is equipped with a temperature control means whereby unconverted oligomer accumulating therein can be maintained molten at a non-depolymerizing temperature. In another aspect, the receiver is also equipped with means for removing molten oligomer from the receiver and, if desired, recycling it to the column via the oligomer feed inlet.

In another aspect of the invention, the oligomer feed rate and the column temperature are coordinated such that from about 50 to 90% of the oligomer, preferably 70 to 80%, is converted to a vapor product stream. In a more specific aspect, the reactor is a sieve tray column and the feed and temperature conditions are maintained such that the rate of formation of the cyclic ester is high enough relative to the column's hydraulic characteristics so that a substantial portion of the oligomer is held in the column, i.e., on the trays, by the cyclic ester vapor bubbling up through the interslices or the holes of the sieve plates.

In preferred aspects the oligomer is an oligomer of lactic acid, more preferably the L-isomer, and the cyclic ester is preferably a lactide, i.e., L-lactide, D-lactide, meso-lactide or a mixture of any two or more thereof, more preferably the L-isomer.

DESCRIPTION OF THE PREFERRED EMBODIMENTS

The invention is directed to a process for preparing a cyclic ester having the formula:

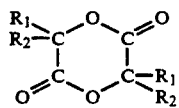

wherein $R_1$ and $R_2$ are independently hydrogen or an aliphatic hydrocarbyl radical having 1 to 6 atoms. According to a key aspect of the process, an oligomer of an alpha-hydroxycarboxylic acid is introduced into a reaction zone maintained at a reduced pressure and an elevated temperature such that the oligomer is depolymerized to form (a) a vapor product stream containing the cyclic ester, which is recovered overhead and (b) an unconverted oligomer stream, which is removed from the lower end of the reaction zone and is maintained at temperatures below depolymerization temperatures.

The vapor product stream may be recovered by any suitable method which does not adversely affect the cyclic ester. For example, the product stream may be condensed, and this may be followed by one or more of redistillation, extraction and/or crystallization from a solvent to recover the desired cyclic ester product.

The oligomeric feed material may comprise an oligomer of an oligomerizable alpha-hydroxycarboxylic acid having the formula:

$$H[OCR_1R_2CO]_nOH,$$

wherein n is an integer of 2 to 30, preferably 5 to 15, and $R_1$ and $R_2$ are independently H or a $C_1$ to $C_6$ hydrocarbyl radical; preferably, $R_1$ and $R_2$, when other than H in the above formula are alkyl groups. More preferably, $R_1$ and $R_2$ are H or methyl, as in glycolic acid ($R_1=R_2=H$) and lactic acid ($R_1=H$, $R_2=$methyl).

The degree of acceptable polymerization (i.e., the value of n) and the resultant molecular weight can vary widely so long as the oligomer may be rendered molten and depolymerized at the operating temperature. For best results, the value of n is in the range of from about 10 and 15. The value of n tends to increase during the course of the depolymerization reaction so that any heel (i.e., polymeric residue) remaining upon completion of the reaction usually has a greater degree of polymerization than the starting oligomer. However, it is a feature of this invention that the oligomeric heel recovered in accordance with the invention has a sufficiently low value of n that it can be recycled directly to the reactor for conversion to additional quantities of the cyclic ester.

The process of this invention is generally conducted in the presence of a catalyst, which may be carried in the oligomeric reactant before it is fed to the reactor. The catalyst can be any catalyst which is suitable for promoting the thermolysis of the oligomers to cyclic esters. Suitable catalysts are generally metals or compounds of metals of groups IV, V and VIII of the Periodic Table. Preferred are metals of groups IV, notably Sn as the metal (powdered), oxide, halogenide or carboxylate, or V, notably Sb, usually as the oxide $Sb_2O_3$. Preferred herein are Sn (II) carboxylates, especially those that are soluble in the molten oligomer and exemplified by stannous bis(2-ethylhexanoate), commonly referred to as stannous octoate.

The catalyst will be employed in catalytically-effective amounts, which can vary widely depending upon the particular feed material employed and the reaction conditions. The optimum catalytically-effective amounts for any particular system can readily be determined through trial runs. For example, with stannous octoate as the catalyst, the quantity of catalyst will generally be such that the reaction mass contains from about 0.01 to about 5% by weight, usually from about 0.3 to 3% and for best results, at least about 1%. High catalyst loadings are desirable because oligomer residence time decreases with increases in the initial catalyst concentration, thereby improving the dimeric cyclic ester production rate.

Suitably effective temperatures for converting oligomer to cyclic ester can vary widely, but normally will be in the range of from about 185° to 270° C., preferably in the range of from about 200° to 220° C. The optimum temperature for any particular oligomer-to-cyclic ester conversion will vary with composition. For example, the production of L- or D-lactide the temperature will preferably range from about 190° to 220° C., for glycolide 220° to 250° C.

The pressure may vary widely from as low as it is practical to attain under industrial conditions to as high as about 50 mm Hg. Preferably, the pressure will be in the range of from about 5 to 25 mm Hg.

The reactor design and configuration are not critical provided there are means for introducing a molten oligomer feed to the depolymerization zone, means for heating the depolymerization zone, means for removing a vapor product stream comprising the cyclic ester to be recovered from the upper end of the reactor and means for collecting unconverted oligomer, if any, from the lower end of the reactor. The reactor may be an unpacked heated column having oligomer feed means at its upper end and means for distributing the oligomer over the heated column surface. Preferably, the column is equipped with means for distributing the oligomer over a wide surface area. Thus, it may be a packed column wherein the packing as well as the column wall can be heated. Or, it may be a multi-stage sieve tray columnar reactor wherein trays contain heating elements, e.g., immersion coils, so that the oligomer on the trays as well as on the wall is heated to depolymerization temperatures.

In operation, molten oligomer fed to the top of the vertically disposed column passes down the column while being heated to depolymerization temperatures. As the oligomer moves down the column at least a portion of it is converted to the more volatile dimeric cyclic ester, which vaporizes and moves up the column. The cyclic ester vapors, moving counter-current to the downcoming and still incompletely converted oligomer, are in equilibrium contact with the oligomer and help keep oligomer on the heated surfaces, e.g., packing material, sieve trays or the like material providing an internal high surface area for the depolymerization reaction. The heat input and the temperature within the reaction zone, hence the rate at which cyclic ester vapors are generated, can be controlled such that the normal tendency for the molten oligomer to drain rapidly down through the column can be held to a practical minimum and the conversion to cyclic ester can be maintained high. In this connection, it is best to start up the reactor by first feeding molten oligomer at a column temperature somewhat below depolymerization temperatures so that the column packing sieve trays are substantially fully loaded before the column is heated to depolymerization temperatures.

The vapor product stream exiting the reactor normally comprises the dimeric cyclic ester and other volatiles, including open-chain hydroxycarboxylic acids (e.g., lactic acid, lactoyllactic acid, etc.). The condensed vapor product is readily separated into its constituents using methods such as distillation, extraction, crystallization, etc.

The unconverted, i.e., incompletely converted oligomer stream exiting the lower end of the reactor is recovered and maintained at temperatures below depolymerization temperatures, thus is kept from continuing to degrade and/or polymerize. It is generally lighter in color, has a lower degree of polymerization and is less viscous than such material that has been subjected to the thermal stress of being heated at depolymerization temperatures throughout the entire reaction period. The recovered oligomer is often sufficiently fluid and has a low enough degree of polymerization to serve as feed stock to the depolymerizer, preferably in admixture with lower molecular weight material.

The following Examples are intended to illustrate, not limit the invention in any way. Temperatures are in degrees Celsius and percentages in percent by weight unless otherwise stated.

EXAMPLE 1

This Example illustrates the cracking/depolymerization of an oligomer of L-lactic acid to form a vapor stream containing L-lactide followed by recovery of the lactide by distillation means.

A. Oligomer Cracking

An oligomer of L-lactic acid was prepared by heating 88% L-lactic acid containing 0.3 percent stannous octoate at temperatures up to 180° with removal of water until the product had a degree of polymerization of about 12. The still molten 150° oligomer was continuously cracked by feeding it to the top of a 7.62 cm diameter 5-sieve tray glass Oldershaw column heated to 210° and maintained at a reduced pressure of 10 mm Hg. The oligomer feed rate was adjusted to allow about 1,437 gms to be fed over a period of about 150 minutes. The oligomer cracked as it moved down the column, and lactide along with other volatile products were vaporized and passed out the top of the column as a continuous vapor product stream. Unvaporized material exited the lower end of the column and accumulated as a heel in a receiver maintained at a temperature below cracking temperatures. About 45% of the oligomer was cracked under the above conditions.

B. Distillative Refining of the Vapor Product Stream

The vapor product stream from the above cracking step was continuously fed to the bottom of a single stage flash distillation zone consisting essentially of a jacketed 18 cm high by 15 cm diameter cylindrical chamber heated at 132° by circulating hot oil and maintained at a pressure of 10 mm Hg. This resulted in the partial condensation of the vapor feed to a crude L-lactide liquid phase (about 70–80% of the feed) and an acid-rich overhead vapor phase (about 20–30%) of the feed which was removed and condensed in cold traps.

The crude L-lactide-rich condensate can be further purified by fractional distillation under reduced pressure at temperatures below about 180° C. for best results.

EXAMPLE 2

This Example illustrates the cracking/depolymerization of an oligomer of L-lactic acid to form an impure L-lactide vapor stream and partial condensation of the vapor stream to obtain a high lactide content condensate, followed by fractional distillation of the condensate to recover low acid content L-lactide.

The general procedure of Example 1 was repeated except that (1) the oligomer had a degree of polymerization of 10. About 1,437 gms of the oligomer was fed to the cracking column over a 2.5 hour period, during which time about 71% of the oligomer was cracked to vaporized products.

Partial condensation of the vapor product stream at 132° and 10 mm Hg pressure gave an acid-rich vapor (about 172 gms) and 843 grams of lactide-rich condensate containing 300 meq/kg of acidity corresponding to 253 meq of acidity. The condensate was immediately solidified by cooling at −10° for overnight storage.

The 843 gms of frozen condensate was liquified by microwave heating and then batch-distilled in a 5.1 cm diameter 20 plate Oldershaw column at 5 mm Hg, a 4:1 to 6:1 reflux radio, a bottoms temperature of 155°–157°, and a head temperature of 119°–124° over a 2.5 hour period. Five overhead cuts were taken as follows:

| Cut | Weight | Acidity |
| --- | --- | --- |
| 1 | 6.1 gms | 674.8 meq/kg |
| 2 | 60.1 | 240 |
| 3 | 185.1 | 69 |
| 4 | 74.6 | 17.4 |
| 5 | 174.7 | 7.4 |
| Heel | 278.4 | 559 |

Having thus described and exemplified the invention with a certain degree of particularity, it should be appreciated that the following claims are not to be so limited but are to be afforded a scope commensurate with the wording of each element of the claim and equivalents thereof.

We claim:

1. In a process for depolymerizing a depolymerizable oligomer of an alpha-hydroxycarboxylic acid of the formula $H(OCR_1R_2CO)_nOH$, where $R_1$ and $R_2$ are independently hydrogen or $C_1$ to $C_6$ alkyl groups and n has a value of from 2 to 30, to a dimeric cyclic ester of the formula

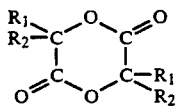

which process involves heating the oligomer under reduced pressure in the substantial absence of a stream of gaseous entraining agent for the cyclic ester at a temperature below the decomposition temperature of the cyclic ester, wherein the improvement comprises the steps of:

(a) providing a multistaged depolymerizing column having heating means, an oligomer feed inlet near the upper end of the column, a vapor product stream outlet above the oligomer feed inlet and a receiver vessel at the lower end of the column;

(b) feeding the oligomer to the upper end of the column;

(c) heating the column to a temperature of about 185° C. to 270° C.;

(d) maintaining the receiver vessel at a temperature below the depolymerization temperature of said oligomer;

(e) coordinating the oligomer feed rate to the column with the column temperature such that a fraction of the oligomer is converted to a vapor product stream containing the cyclic ester and another fraction of the oligomer is allowed to exit the column at its lower end and pass to the receiver vessel; and, (f) removing the vapor product stream through the outlet at the upper end of the column and recovering the cyclic ester therefrom.

2. The process of claim 1 wherein the receiver vessel is equipped with a temperature control means and the vessel is maintained thereby at a non-depolymerizing temperature at which the oligomer therein is molten.

3. The process of claim 1 wherein a portion of the oligomer in the receiver vessel is removed and recycled to the oligomer feed inlet of the column.

4. The process of claim 1 wherein the oligomer feed rate and the column temperature are coordinated such that from about 50 to 90 percent by weight of the oligomer is converted to a vapor product stream.

5. The process of claim 4 wherein about 70 to 80 percent of the oligomer is converted.

6. The process of claim 5 wherein each $R_1$ and $R_2$ in the oligomer and cyclic ester is at least one of hydrogen and methyl.

7. The process of claim 6 wherein each of $R_1$ and $R_2$ is hydrogen the cyclic ester is glycolide and the column is heated to about 220° to 260° C.

8. The process of claim 6 wherein $R_1$ in all occurrences is hydrogen and $R_2$ in all occurrences is methyl, the cyclic ester is a lactide and the column is heated to about 190° to 220° C.

9. The process of claim 8 wherein the lactide is L-lactide, D-lactide, meso-lactide or a mixture of any two or more thereof.

10. The process of claim 8 wherein the lactide is L-lactide.

11. The process of claim 1 additionally comprising the step of purifying the recovered cyclic ester by fractional distillation.

12. The process of claim 1 wherein the cyclic ester is recovered from the vapor product stream by partial condensation.

13. The process of claim 12 additionally comprising the step of purifying the recovered cyclic ester by fractional distillation.

14. The process of claim 13 wherein the cyclic ester is lactide.

* * * * *